(12) United States Patent
Hwang et al.

(10) Patent No.: US 11,650,255 B2
(45) Date of Patent: May 16, 2023

(54) CHAMBER AND SYSTEM FOR REAL-TIME ANALYSIS OF GAS GENERATED INSIDE SECONDARY BATTERY

(71) Applicant: LG Chem, Ltd., Seoul (KR)

(72) Inventors: Dongguk Hwang, Daejeon (KR); Jeong Ae Ahn, Daejeon (KR); Nak Hee Choi, Daejeon (KR)

(73) Assignee: LG Energy Solution, Ltd.

( * ) Notice: Subject to any disclaimer, the term of this patent is extended or adjusted under 35 U.S.C. 154(b) by 249 days.

(21) Appl. No.: 16/758,449

(22) PCT Filed: Jun. 5, 2019

(86) PCT No.: PCT/KR2019/006801
§ 371 (c)(1),
(2) Date: Apr. 23, 2020

(87) PCT Pub. No.: WO2019/235844
PCT Pub. Date: Dec. 12, 2019

(65) Prior Publication Data
US 2020/0256921 A1      Aug. 13, 2020

(30) Foreign Application Priority Data

Jun. 7, 2018 (KR) ......................... 10-2018-0065250
Oct. 30, 2018 (KR) ......................... 10-2018-0130857

(51) Int. Cl.
*G01R 31/374* (2019.01)
*H01M 10/42* (2006.01)
(Continued)

(52) U.S. Cl.
CPC ............. *G01R 31/374* (2019.01); *G01N 1/24* (2013.01); *G01N 33/0036* (2013.01);
(Continued)

(58) Field of Classification Search
None
See application file for complete search history.

(56) References Cited

U.S. PATENT DOCUMENTS

2001/0016278 A1    8/2001  Onishi et al.
2013/0280575 A1*  10/2013  Obrist ................ H01M 10/647
                                                429/120
(Continued)

FOREIGN PATENT DOCUMENTS

CN        202268405 U      6/2012
CN        103326084 A      9/2013
(Continued)

OTHER PUBLICATIONS

Schaevitz et al.; High Temperature Fuel Cell Device And Management Of Heat Quantity, Reactant And Security Thereof; Date Published: Aug. 20, 2008; CN 101248550 A; H01M8/04432 (Year: 2008).*

(Continued)

*Primary Examiner* — Nasima Monsur
(74) *Attorney, Agent, or Firm* — Lerner David LLP

(57) ABSTRACT

A chamber and a system for real-time analysis of gas generated inside a secondary battery. The chamber and system are capable of adjusting temperature while directly applying heat to the secondary battery. The system may include a chamber, a pump module, and an analysis module. The chamber may include a first housing which is insulative, and configured to house the secondary battery mounted in an inner space surrounded by the first housing, a second housing which is thermally conductive and surrounding the first housing, an inlet connected to the pump module, a temperature sensor configured to measure a temperature of the secondary battery or a temperature inside the chamber, and a first heat generation member configured to heat the sec- (Continued)

ondary battery, the first heat generation member being configured to be inserted into the second housing.

10 Claims, 5 Drawing Sheets

(51) Int. Cl.
   *H01M 10/46* (2006.01)
   *G01N 1/24* (2006.01)
   *G01N 33/00* (2006.01)
   *G05D 23/19* (2006.01)
(52) U.S. Cl.
   CPC ....... *H01M 10/4285* (2013.01); *H01M 10/46* (2013.01); *G05D 23/19* (2013.01)

(56) References Cited

U.S. PATENT DOCUMENTS

2014/0174084 A1    6/2014   Kontomaris
2014/0342195 A1*  11/2014   Bhola ................ H01M 10/647
                                                            429/50

FOREIGN PATENT DOCUMENTS

| | | |
|---|---|---|
| CN | 103411795 A | 11/2013 |
| CN | 203587168 U | 5/2014 |
| CN | 205985250 U | 2/2017 |
| CN | 207572483 U | 7/2018 |
| JP | S57048635 A | 3/1982 |
| JP | H04113249 A | 4/1992 |
| JP | 2001236986 A | 8/2001 |
| JP | 2011003513 A | 1/2011 |
| JP | 2011134598 A | 7/2011 |
| JP | 2012058180 A | 3/2012 |
| JP | 2016051683 A | 4/2016 |
| JP | 2016118395 A | 6/2016 |
| JP | 2017181212 A | 10/2017 |
| JP | 2017181324 A | 10/2017 |
| KR | 20140054252 A | 5/2014 |
| KR | 101454252 B1 | 10/2014 |
| KR | 20160008409 A | 1/2016 |
| KR | 20160066909 A | 6/2016 |
| KR | 20160072571 A | 6/2016 |
| KR | 20160144217 A | 12/2016 |
| KR | 20180047359 A | 5/2018 |
| WO | 2006088021 A1 | 8/2006 |

OTHER PUBLICATIONS

International Search Report for PCT/KR2019/006801 dated Oct. 4, 2019; 2 pages.

* cited by examiner

[Fig. 1]
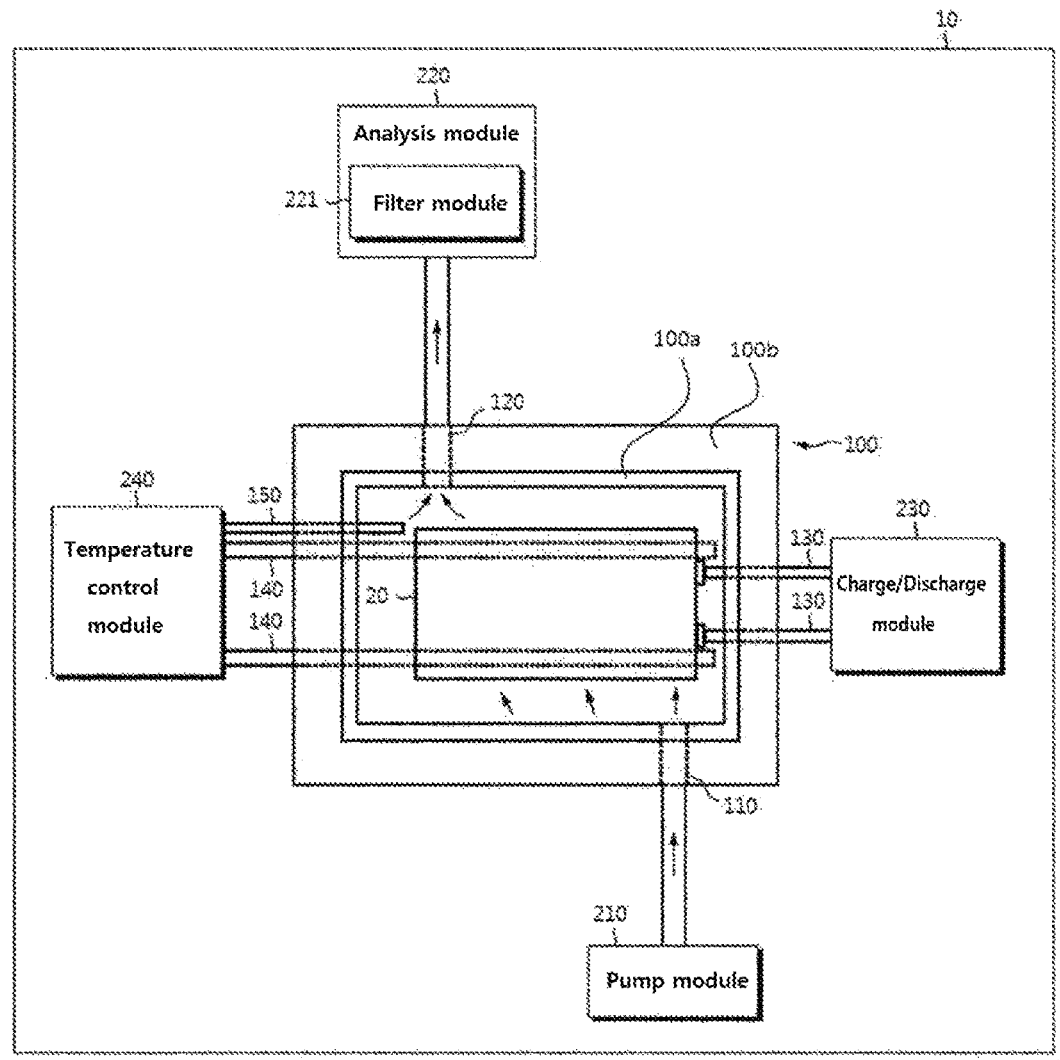

[Fig. 2]
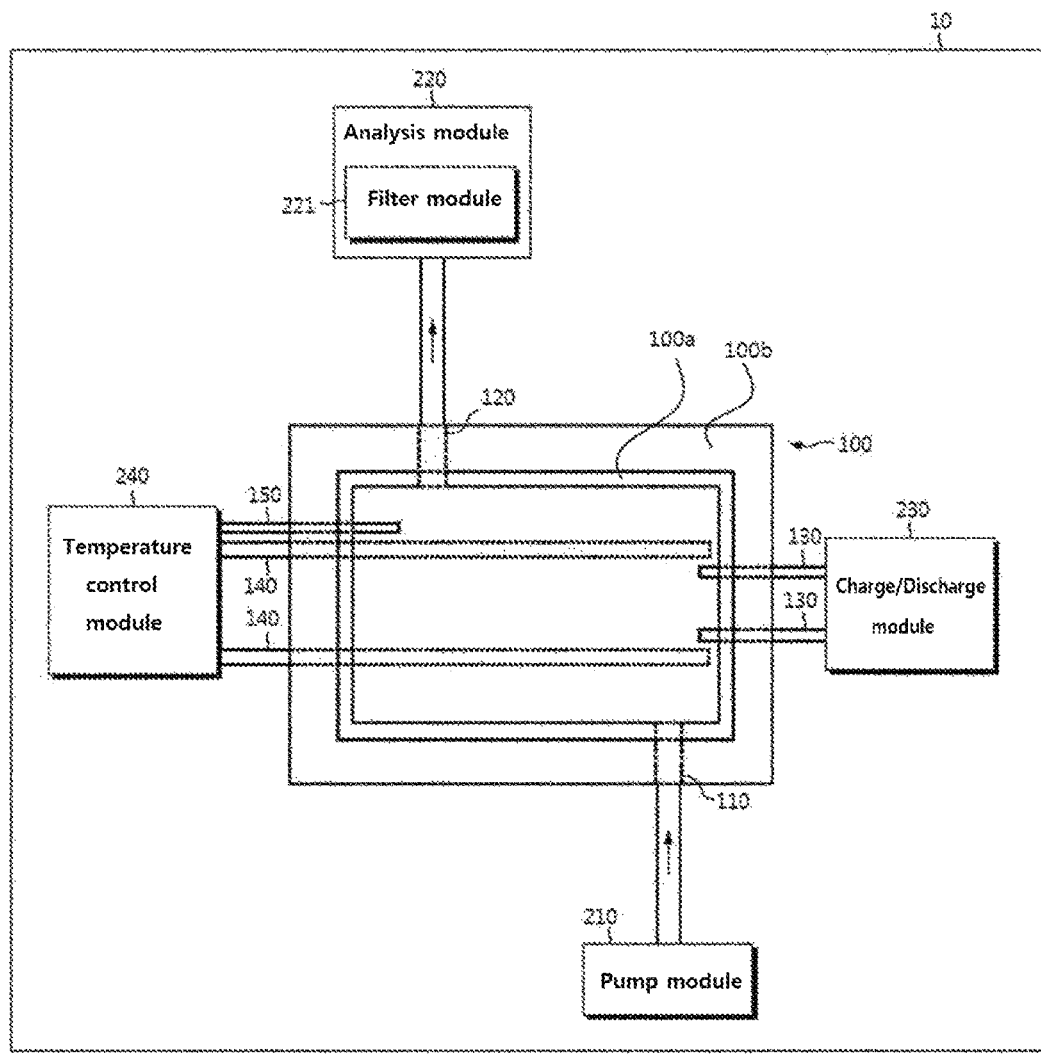

[Fig. 3]
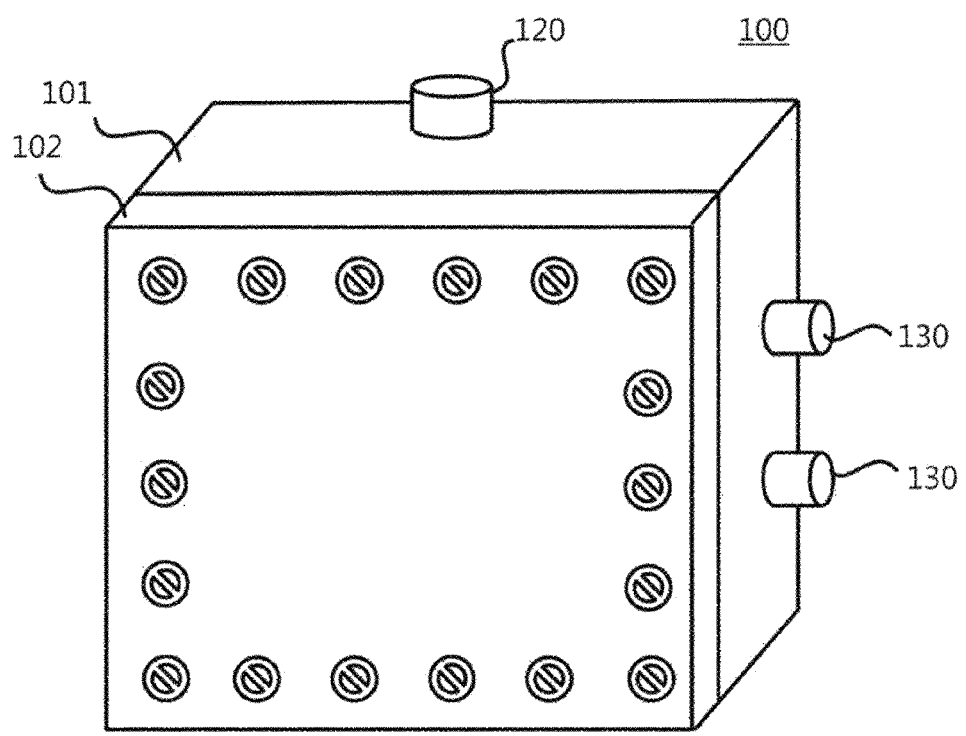

[Fig. 4a]
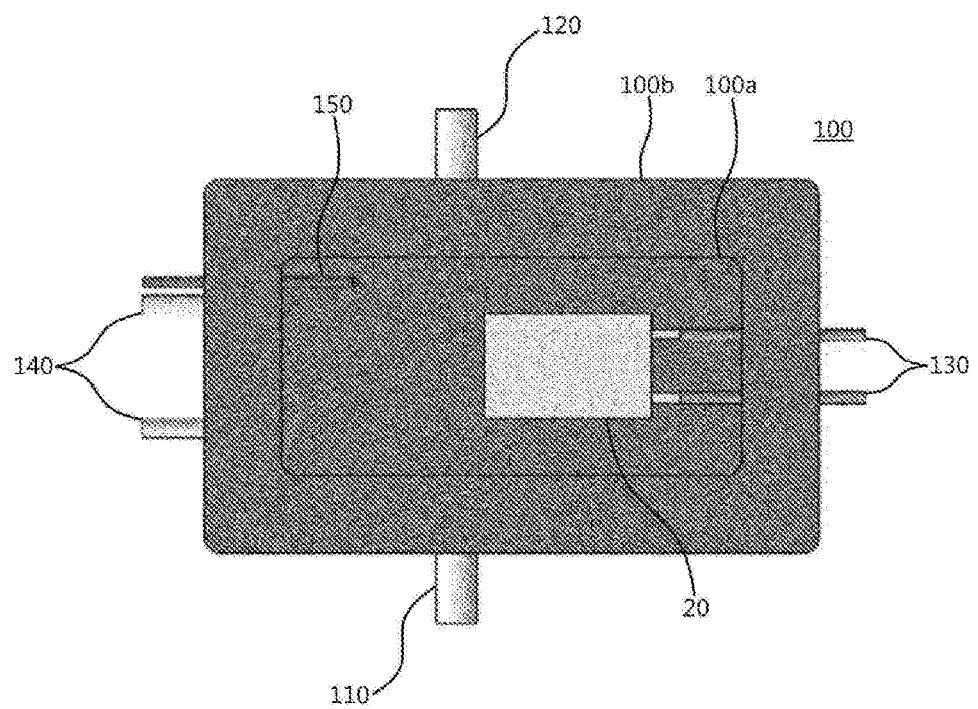

[Fig. 4b]
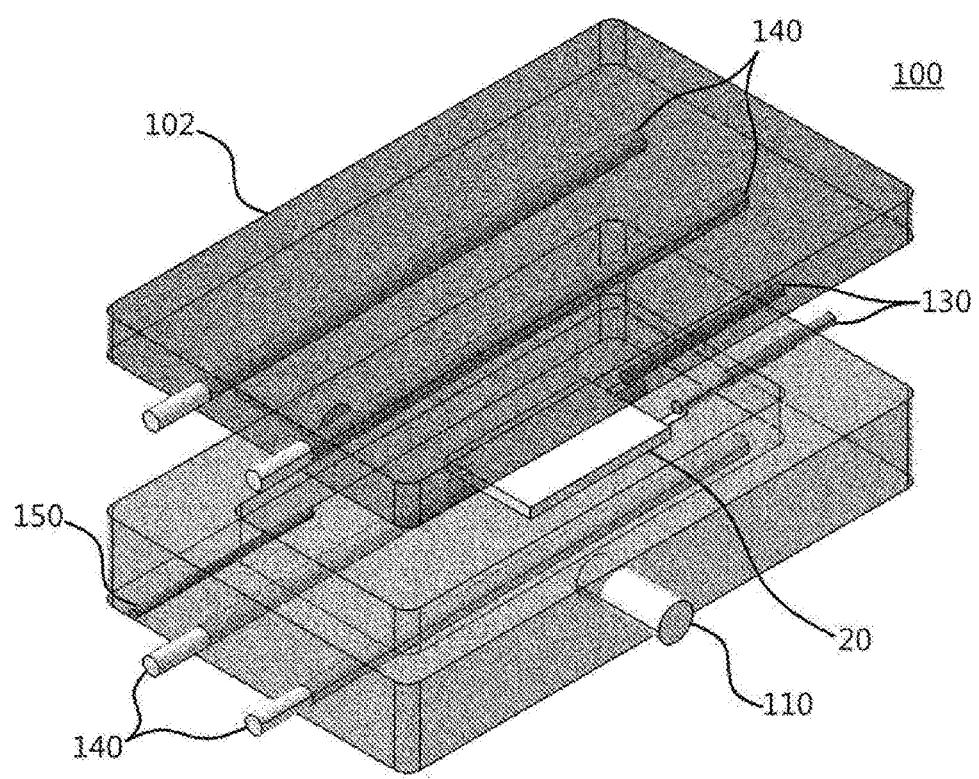

CHAMBER AND SYSTEM FOR REAL-TIME ANALYSIS OF GAS GENERATED INSIDE SECONDARY BATTERY

BACKGROUND OF THE INVENTION

1. Field of the Invention

This application claims the benefit of priorities to Korean Patent Application Nos. 10-2018-0065250, filed on Jun. 7, 2018 and 10-2018-0130857, filed on Oct. 30, 2018, the entire disclosures of which are incorporated herein by reference.

The present invention relates to a chamber and a system for real-time analysis of a generated gas in a secondary battery, and more particularly, to a chamber and a system for real-time analysis of a generated gas in a secondary battery in which heat can be directly applied to the second battery with control.

2. Description of the Related Art

In general, a secondary battery is a battery that can be repeatedly used through a discharge process of converting chemical energy into electrical energy and a charging process in the reverse direction thereof. The secondary battery having electric properties such as high application ability to product groups and high energy density is commonly used in electric vehicles (EVs) or hybrid vehicles (HVs) driven by electric driving sources as well as portable devices.

In collecting and analyzing the generated gas in the secondary battery, various gases are generated during operation of the secondary battery. The information on the composition and content of the generated gas in the secondary battery may be used for developing battery materials, optimizing battery manufacturing processes, and identification of the cause of battery failure.

However, in a conventional chamber for analyzing the gas generated in the secondary battery, in order to perform a gas generation analysis according to the temperature difference in the battery, the chamber is heated with an external heating device such as an oven in which the entire chamber can be included to raise the temperature of the chamber, thereby raising the temperature of the battery in the chamber. Such a conventional chamber has a limitation that it is not possible to apply temperature directly to the battery in order to analyze the gas generated in the battery in the study of the high temperature characteristic of the battery. There is a disadvantage that it is not possible to apply the exact temperature desired to the battery because it does not directly heat the battery. In addition, due to the specific heat characteristics of the chamber material, a long time for the temperature rise is required.

SUMMARY OF THE INVENTION

Therefore, the present invention is to solve the above problems. An object of the present invention is to provide a chamber for real-time analysis in which a basic role of the chamber is performed, temperature is directly applied to the battery and the temperature to be applied to the battery is controlled.

A chamber for real-time analysis of the generated gas in the secondary battery according to the present invention comprises:

a first housing which is insulative, wherein a secondary battery is mounted in an inner space surrounded by the first housing;

a second housing which is thermally conductive and surrounding the first housing;

an inlet for connecting a pump module for generating a flow of an induction medium into the chamber, and an outlet for connecting an analysis module for analyzing the generated gas in the secondary battery by the flow of the induction medium;

a temperature sensor for detecting temperature of the secondary battery or temperature inside the chamber; and a heating member for heating to the secondary battery, wherein the heating member is inserted in the second housing.

In addition, a system for real-time analysis of the generated gas in the secondary battery according to the present invention comprises:

a chamber for real-time analysis of a generated gas in a secondary battery;

a pump module for generating a flow of an induction medium into the chamber;

an analysis module for analyzing the generated gas in the secondary battery introduced from the chamber by the flow of the induction medium; and a temperature control module for measuring temperature of the secondary battery or temperature inside the chamber by a temperature sensor and for controlling the temperature applied to the secondary battery by a heating member to a desired temperature in real time, wherein the temperature sensor and the heating member are connected to the temperature control module, respectively.

EFFECT OF THE INVENTION

In the chamber according to the present invention a basic role of the chamber for real-time gas analysis can be performed, and in addition thereto, temperature can be directly applied to the secondary battery and the temperature applied to the secondary battery can be controlled. Accordingly, it is possible to precisely analyze the composition and the relative amount change of the generated gas according to the temperature characteristics of the battery. In addition, there is an advantage that can be utilized in analyzing the gas generated in the secondary battery with regard to high temperature characteristics of the secondary battery. In addition, it is possible to increase the temperature of the secondary battery in a short time (for example, within a few seconds) via direct application of heat to the secondary battery, by improving that a long time for temperature rise is required due to specific heat characteristics of the conventional chamber material. Therefore, there is an advantage of analyzing the gas generated in the secondary battery quickly and efficiently.

BRIEF DESCRIPTION OF THE DRAWINGS

FIGS. 1 and 2 are schematic diagrams of a system 10 for real-time analysis of a generated gas in a secondary battery, comprising a chamber 100 for real-time analysis of a generated gas in a secondary battery according to the present invention, showing a case where a secondary battery 20 is mounted and a case where a secondary battery 20 is not mounted, respectively.

FIG. 3 is a schematic external perspective view of the chamber 100 for analysis of the generated gas in the secondary battery of FIG. 1.

FIGS. 4a and 4b are a front view and a perspective view schematically illustrating an inside of the chamber 100 for analysis of the generated gas in the secondary battery of FIG. 1, respectively.

DETAILED DESCRIPTION OF THE INVENTION

A chamber for real-time analysis of the generated gas in the secondary battery according to the present invention comprises:

a first housing which is insulative, wherein a secondary battery is mounted in an inner space surrounded by the first housing;

a second housing which is thermally conductive and surrounding the first housing;

an inlet for connecting a pump module for generating a flow of an induction medium into the chamber, and an outlet for connecting an analysis module for analyzing the generated gas in the secondary battery by the flow of the induction medium;

a temperature sensor for detecting temperature of the secondary battery or temperature inside the chamber; and a heating member for heating to the secondary battery, wherein the heating member is inserted in the second housing.

In addition, in the chamber for real-time analysis of the generated gas in the secondary battery according to the present invention, the heating member may have a bar shape.

In addition, in the chamber for real-time analysis of the generated gas in the secondary battery according to the present invention, the first housing may be made of Teflon, bakelite, or rubber, the second housing may be made of stainless steel, copper, or aluminum, and the heating member may be made of nickel, chromium, or aluminum.

In addition, in the chamber for real-time analysis of the generated gas in the secondary battery according to the present invention, the chamber may further comprise charging/discharging terminals for contacting electrodes of the secondary battery, to cause a charge/discharge module to charge/discharge the secondary battery, wherein the charge/discharge module is electrically connected to electrodes of the secondary battery to drive a charge/discharge of the secondary battery.

In addition, in the chamber for real-time analysis of the generated gas in the secondary battery according to the present invention, one end of the temperature sensor may be located close to the secondary battery or in contact with the secondary battery to measure temperature of the secondary battery.

In addition, in the chamber for real-time analysis of the generated gas in the secondary battery according to the present invention, the chamber may have at least two heating members and the heating members may be inserted into one surface of the second housing, wherein one of the heating members may be inserted into an upper portion of one surface of the second housing, and the other of the heating members may be inserted into a lower portion of one surface of the second housing.

In addition, in the chamber for real-time analysis of the generated gas in the secondary battery according to the present invention, the chamber may have at least two heating members and some of the heating members may be inserted into any one surface of two opposite surfaces of the second housing, and the others of the heating members may be inserted into the other surface of the two opposite surfaces of the second housing.

In addition, in the chamber for real-time analysis of the generated gas in the secondary battery according to the present invention, the chamber may comprise a chamber body which has a cuboid shape with an open one surface and a chamber cover coupled to the open one surface of the chamber body, wherein the chamber body and the chamber cover may be combined to form a space in which the secondary battery is mounted and the heating member may be inserted into the second housing of the chamber body.

In addition, in the chamber for real-time analysis of the generated gas in the secondary battery according to the present invention, the chamber may have a plurality of heating members, and some of the heating members may be inserted into the second housing of the chamber body, and the others of the heating members may be inserted into the second housing of the chamber cover.

In addition, a system for real-time analysis of the generated gas in the secondary battery according to the present invention comprises:

a chamber for real-time analysis of a generated gas in a secondary battery;

a pump module for generating a flow of an induction medium into the chamber;

an analysis module for analyzing the generated gas in the secondary battery introduced from the chamber by the flow of the induction medium; and a temperature control module for measuring temperature of the secondary battery or temperature inside the chamber by a temperature sensor and for controlling the temperature applied to the secondary battery by a heating member to a desired temperature in real time, wherein the temperature sensor and the heating member may be connected to the temperature control module, respectively.

The system for real-time analysis of the generated gas in the secondary battery according to the present invention may further comprise a charge and discharge module which is electrically connected to electrodes of the secondary battery to drive a charge/discharge of the secondary battery.

Hereinafter, the chamber for real-time analysis of the generated gas in the secondary battery according to an embodiment of the present invention will be described in detail. The accompanying drawings show exemplary forms of the present invention, which are provided to explain the present invention in more detail, and the technical scope of the present invention is not limited thereto.

In addition, irrespective of the graphic symbols, the same or corresponding components will be given for the same reference numerals, and redundant description thereof will be omitted and for the convenience of description, the size and shape of each component shown may be exaggerated or reduced.

FIG. 1 is a schematic diagram of a system 10 for analysis of a generated gas in a secondary battery comprising a chamber 100 for analysis of a generated gas in a secondary battery according to the present invention. FIG. 2 shows a case where a secondary battery 20 is not mounted in the system 10 for analysis of a generated gas in a secondary battery comprising the chamber 100 for analysis of a generated gas in a secondary battery of FIG. 1.

First, referring to FIG. 1, the system 10 for real-time analysis of the generated gas in the secondary battery comprises a chamber 100 in which the secondary battery 20 is mounted, a pump module 210, and an analysis module 220.

The secondary battery 20 may be a can type (cylindrical, square, etc.), pouch type, or coin cell type secondary battery. The secondary battery 20 may be charged or discharged by an electrochemical reaction of an active material, a metal plate, and an electrolyte, and the like. During such charge or discharge driving, an internal gas may be generated by internal electrochemical reactions.

The secondary battery 20 may be mounted in the chamber 100. The chamber 100 may have a dual structure, i.e., a first housing 100a and a second housing 100b surrounding the first housing 100a. The secondary battery 20 may be mounted in a space surrounded by the first housing 100a.

The first housing 100a may be formed of an insulating material, for example, Teflon, bakelite, or rubber. Accordingly, it is possible to prevent electricity from flowing directly to the secondary battery 20 through components other than the charging and discharging terminals 130 that are in contact with the terminals of the secondary battery 20. The second housing 100b may be formed of a thermally conductive material, for example, a metal material such as stainless steel, copper, or aluminum. The first housing 100a and the second housing 100b may be integrally formed or may be separated from each other.

In addition, such a chamber 100 may be composed of a chamber body 101 and a chamber cover 102 which are separated and coupled to each other, as shown in FIG. 3. In other words, the chamber body 101 may be provided, for example, in a cuboid shape with an open front portion, and the chamber cover 102 may be provided to shield the opening of the chamber body 101. When the chamber body 101 and the chamber cover 102 are coupled, they may be formed in the structure having the first housing 100a in which the secondary battery 20 is mounted and the second housing 100b surrounding the first housing 100a, as described above.

More specifically, the chamber body 101 may have a dual structure, i.e., a first housing 100a in which the secondary battery 20 is mounted and which has an open front portion and a second housing 100b which surrounds the first housing 100a and similarly has an open front portion. Like the chamber body 101, the chamber cover 102 may have a dual structure, i.e., a first housing 100a of the chamber cover covering the first housing 100a of the chamber body 101 and a second housing 100b of the chamber cover covering the second housing 100b of the chamber body 101.

The chamber body 101 and the chamber cover 102 may be tightly coupled by fixing means such as fixing pins, screws and bolts. The contact surface between the chamber body 101 and the chamber cover 102 may further comprise a sealing member such as an O-ring for sealing when the chamber body 101 and the chamber cover 102 are coupled to each other.

The chamber 100 is provided with an inlet 110 through which the pump module 210 can be connected and an outlet 120 through which the analysis module 220 can be connected.

Referring to FIG. 1, the pump module 210 introduces an induction medium comprising an inert gas or the like into the chamber 100 through the inlet 110 provided in the chamber 100. The pump module 210 includes a device for moving a gas medium such as a mass flow meter (MFC), and the like. The pump module 210 is connected to the inlet 110 via an induction pipe so that gas flow can be generated. The induction medium comprising an inert gas or the like is preferably composed of an inert gas such as helium, nitrogen, argon, etc. However, the gas component constituting the induction medium may be appropriately selected depending on the component of the generated gas in the secondary battery to be detected and the purpose of analyzing the generated gas in the secondary battery.

By controlling flow rate in the pump module 210, the induction medium may be strongly introduced into the chamber 100, and the induction medium introduced into the chamber 100 exit the chamber 100 through the outlet 120 due to the pressure difference between the inlet 110 and the outlet 120 of the chamber 100. By such a transfer flow of the induction medium, the generated gas in the secondary battery 20 is transferred to the analysis module 220 through the outlet 120 together with the induction medium.

The analysis module 220 is connected to the outlet 120 provided in the chamber 100 by an induction pipe so that a moving flow of gas discharged from the outlet 120 provided in the chamber 100 can be generated. The analysis module 220 may comprise a filter module 121 for filtering the induction medium. FIG. 1 and FIG. 2 illustrate the case in which the analysis module 220 is connected to the chamber 100 through the induction pipe. If desired, a gas collecting tube (not shown) for collecting the generated gas in the secondary battery may be connected to the outlet 120, and after the collection of the generated gas in the secondary battery, the gas collecting tube may be connected to the analysis module 220 to perform the analysis.

In addition, the chamber 100 may further comprise charging/discharging terminals 130 for contacting electrodes of the secondary battery 20, to cause a charge/discharge module 230 to charge/discharge the secondary battery. The charge/discharge module 230 is electrically connected to electrodes of the secondary battery 20 to drive a charge/discharge of the secondary battery 20. The charge/discharge module 230 includes a power supply unit, a load unit, and a switching circuit. The power supply unit regulates the voltage and/or current to charge the secondary battery 20, and the load unit discharges the energy charged in the secondary battery 20. The power supply unit and the load unit may be electrically connected to the secondary battery 20 through the charging/discharging terminals 130. The charging/discharging terminals 130 may be provided in the chamber 100. The power supply unit and the load unit may be electrically connected to the secondary battery 20 selectively by a switching circuit. The charge/discharge module 230 may be configured to be controlled by a user signal input through an interface means such as a computer of the user.

In addition, the chamber 100 further comprises a heating member 140 for increasing the temperature inside the chamber and a temperature sensor 150 for measuring the temperature of the secondary battery 20 or the temperature inside the chamber 100.

According to the present invention, the heating member 140 is implemented that can be inserted into the interior of the second housing 100b (that is, not the space surrounded by the second housing 100b, but the second housing 100b itself). More specifically, the heating member 140 may be inserted into the interior of at least one surface of the second housing 100b. As shown in FIG. 4b, the heating member 140 is not exposed to an inner space formed by being surrounded by the first housing 100a, so that the heating member 140 does not directly contact with the secondary battery 20.

However, in the prior art, an oven is provided outside the chamber to increase the chamber temperature and heat is applied to the chamber from the oven provided outside. Therefore, a considerable time was required to increase the temperature of the secondary battery and there was a difficulty in heating the secondary battery to the desired temperature accurately.

As illustrated in FIGS. 1 and 2, the heating member 140 according to the present invention may be implemented in a bar shape. In other words, the heating member 140 may have a bar shape with a high output. FIGS. 1 and 2 illustrate a case in which two heating members 140 are respectively inserted into upper and lower portions of the inside of one surface of the second housing 100b when the pouch-type secondary battery 20 is heated. However, the present invention is not limited to the above. As long as the heating member 140 can be inserted into the second housing 100b to heat the secondary battery 20, the shape, number, and position to be inserted into the second housing 100b of the heating member 140 can be modified and changed. In addition, the heating member 140 may be formed of a thermally conductive material, for example, stainless steel, copper, or aluminum.

In addition, as described above, since the second housing 100b may be formed of a thermally conductive material, for example, a material such as SUS or metal, the second housing 100b can be heated by the heating member 140 inserted into the second housing 100b itself. Accordingly, the secondary battery 20 mounted in the first housing 100a may be heated through the first housing 100a in the second housing 100b.

However, since the insulating first housing 100a is positioned between the second housing 100b heated by the heating member 140 and the secondary battery 20, the heated second housing 100b or the heating member 140 does not directly contact with the secondary battery 20, thereby preventing the risk of explosion and ignition of the secondary battery 20. If the first housing 100a is not provided, the secondary battery 20 is in direct contact with the heated second housing 100b or the heating member 140, and thus there is a risk of safety problems due to shortening of the secondary battery 20. In addition, the first housing 100a is preferably formed as thin as possible so that the heat applied by the second housing 100b in which the heating member 140 is inserted can be sufficiently transferred to the secondary battery 20.

One end of the temperature sensor 150 is exposed to the inner space surrounded by the first housing 100a, and one end of the temperature sensor may be located close to the secondary battery so that the temperature outside the secondary battery 20 (i.e., the temperature inside the chamber 100) can be measured or one end of the temperature sensor may be in contact with the secondary battery so that the temperature of the secondary battery itself can be measured.

The temperature sensor 150 and the heating member 140 are each connected to the temperature control module 240. The temperature control module 240 controls the measurement of the temperature of the secondary battery 20 or the temperature inside the chamber 100 by a temperature sensor 150 and the heating of the secondary battery 20 to a desired temperature by a heating member 140. Therefore, when analyzing the gas generated in the secondary battery 20, the analysis may be performed while controlling the temperature applied to the secondary battery 20 in real time.

The chamber 100 may further comprise a pressure gauge (not shown) for measuring pressure inside the chamber 100.

Meanwhile, in the system for analysis of the generated gas in the secondary battery according to the present invention, the inside of the chamber 100 may be formed in a vacuum state before the experiment so as to derive a more accurate result value. To this end, the system 10 for analysis of the generated gas in the secondary battery may further comprise a vacuum pump (not shown) connected to the chamber 100 to form a vacuum state inside the chamber 100.

FIG. 3 is a perspective view schematically illustrating the outside of the chamber 100 of FIG. 1. As shown in FIG. 3, the heating member 140 may be inserted into one surface of the chamber body 101. However, various modifications and changes are possible, for example, the heating member 140 may be inserted into the chamber cover 102, or the hearing member 140 may be inserted into each of the chamber body 101 and the chamber cover 102. In addition, the heating member 140 may be inserted into not only one surface of the chamber body 101 but also the other surfaces of the chamber body 101.

FIGS. 4a and 4b schematically show the interior of the chamber 100 of FIG. 1. FIGS. 4a and 4b show the case in which the chamber cover 102 of the chamber 100 is separated from the chamber body 101, and the secondary battery 20 is mounted in a space surrounded by the first housing 100a of the chamber body 101. In FIG. 4a, the chamber cover 102 is not shown. The heating member 140 is inserted inside the second housing 100b (i.e., the second housing 100b itself). Meanwhile, in the chamber 100 of FIGS. 4a and 4b, the secondary battery 20 is mounted in a space surrounded by the first housing 100a made of an insulating material, and the first housing 100a is surrounded by the second housing 100b, as described above.

As such, according to the chamber 100 according to the present invention, there are advantages that a basic role of the chamber for real-time gas analysis can be performed, and in addition thereto, temperature is directly applied to the secondary battery and the temperature applied to the secondary battery can be controlled. Accordingly, it is possible to precisely analyze the composition and the relative amount change of the generated gas with regard to the temperature characteristics of the battery. In addition, there is an advantage that it can be utilized in analyzing the gas generated in the secondary battery with regard to high temperature characteristics of the secondary battery. In addition, it is possible to increase the temperature of the secondary battery in a short time (for example, within a few seconds) by directly heating the secondary battery by improving that a long time for temperature rise is required due to specific heat characteristics of the conventional chamber material. Therefore, there is an advantage of analyzing the gas generated in the secondary battery quickly and efficiently.

In addition, since the heating member is inserted into the second housing of the chamber, there is an advantage that the secondary battery can be heated more safely as well as directly and quickly. That is, when the heating member is inserted into the first housing which is in contact with the secondary battery or the heating member is located in the inner space where the secondary battery of the chamber is mounted, there is a concern about explosion of the battery. However, according to the present invention, it is possible to heat the secondary battery quickly while solving the concern about safety problems when the secondary battery is heated.

In the actual experiment using the chamber 100 shown in FIGS. 4a and 4b, only about one minute was required to raise the temperature from room temperature to 60° C. Thus, according to the present invention, it is possible to apply a high temperature directly to the secondary battery in a short time.

It will be appreciated that the technical configuration of the present invention described above may be embodied in other specific forms by those skilled in the art without changing the technical spirit or essential features of the present invention. Therefore, it is to be understood that the embodiments described above are exemplary and not limiting in all respects. In addition, the scope of the present invention is indicated by the appended claims rather than the detailed description above. In addition, it should be construed that all changes or modifications derived from the meaning and scope of the claims and equivalent concepts thereof are included in the scope of the present invention.

INDUSTRIAL AVAILABILITY

In the chamber according to the present invention, a basic role of the chamber for real-time gas analysis can be performed, and in addition thereto, temperature can be directly applied to the secondary battery and the temperature applied to the secondary battery can be controlled. Accordingly, it is possible to precisely analyze the composition and the relative amount change of the generated gas according to the temperature characteristics of the battery. In addition, there is an advantage that it can be utilized in analyzing the gas generated in the secondary battery with regard to high temperature characteristics of the secondary battery. In addition, it is possible to increase the temperature of the secondary battery in a short time (for example, within a few seconds) by directly heating the secondary battery by improving that a long time for temperature rise is required due to specific heat characteristics of the conventional chamber material. Therefore, there is an advantage of analyzing the gas generated in the secondary battery quickly and efficiently.

What is claimed is:

1. A chamber for real-time analysis of a generated gas in a secondary battery, comprising:
    a first housing which is insulative, and configured to house the secondary battery mounted in an inner space surrounded by the first housing;
    a second housing which is thermally conductive and surrounding the first housing;
    an inlet configured to connect a pump module for generating a flow of an induction medium into the chamber, and an outlet for connecting an analysis module for analyzing the generated gas in the secondary battery by the flow of the induction medium;
    a temperature sensor configured to measure a temperature of the secondary battery or a temperature inside the chamber; and
    a first heat generation member configured to heat the secondary battery, wherein the first heat generation member is configured to be inserted into the second housing,
    wherein the first housing is made of Teflon, bakelite, or rubber, the second housing is made of stainless steel, copper, or aluminum, and the first heat generation member is made of nickel, chromium, or aluminum.

2. The chamber according to claim 1, wherein the first heat generation member has a bar shape.

3. The chamber according to claim 1, wherein the chamber further comprises charging/discharging terminals configured to contact electrodes of the secondary battery, wherein the charging/discharging terminals are configured to cause a charge/discharge module to charge/discharge the secondary battery, and wherein the charge/discharge module is configured to be electrically connected to electrodes of the secondary battery in order to drive charging/discharging of the secondary battery.

4. The chamber according to claim 1, wherein the temperature sensor is positioned such that a first end of the temperature sensor is in contact with or within proximity to the secondary battery in order to measure the temperature of the secondary battery.

5. The chamber according to claim 1, wherein the chamber comprises a second heat generation member, wherein the first and second heat generation members are inserted into a surface of the second housing, and wherein the first heat generation member is configured to be inserted into an upper portion of the surface of the second housing and the second heat generation member is configured to be inserted into a lower portion of the surface of the second housing.

6. The chamber according to claim 1, wherein the chamber comprises a second heat generation member, and wherein the first heat generation member is inserted into a first surface of the second housing, and the second heat generation member is inserted into an opposite second surface of the second housing.

7. The chamber according to claim 1, wherein the chamber comprises a chamber body which has a cuboid shape with an opening on one side and a chamber cover coupled to the opening of the chamber body, wherein the chamber body and the chamber cover are combined to form a space in which the secondary battery is mounted and into which the heat generation member is inserted.

8. The chamber according to claim 7, further comprising a second heat generation member, wherein the first heat generation member is inserted into the second housing of the chamber body, and the second heat generation member is inserted into the second housing of the chamber cover.

9. A system for real-time analysis of a generated gas in a secondary battery, comprising:
    the chamber according to claim 1;
    the pump module;
    the analysis module; and
    a temperature control module configured to control a temperature applied to the secondary battery by the first heat generation member in real time,
    wherein the temperature sensor and the first heat generation member are connected to the temperature control module, respectively.

10. The system according to claim 9, wherein the system further comprises a charge/discharge module which is electrically connected to electrodes of the secondary battery to drive a charge/discharge of the secondary battery.

* * * * *